United States Patent
Omae et al.

(10) Patent No.: US 7,803,818 B2
(45) Date of Patent: Sep. 28, 2010

(54) AMORPHOUS FORM OF 1,2-DIHYDROPYRIDINE COMPOUND

(75) Inventors: Takao Omae, Tsukuba (JP); Yukiko Sugaya, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/158,299

(22) PCT Filed: Dec. 20, 2006

(86) PCT No.: PCT/JP2006/325396

§ 371 (c)(1),
(2), (4) Date: Aug. 11, 2008

(87) PCT Pub. No.: WO2007/072869

PCT Pub. Date: Jun. 28, 2007

(65) Prior Publication Data

US 2008/0312284 A1     Dec. 18, 2008

(30) Foreign Application Priority Data

Dec. 21, 2005   (JP) .............................. 2005-368431

(51) Int. Cl.
*A61K 31/444* (2006.01)
*C07D 213/64* (2006.01)

(52) U.S. Cl. ..................................... 514/334; 546/257

(58) Field of Classification Search ................. 546/257; 514/334

See application file for complete search history.

(56) References Cited

U.S. PATENT DOCUMENTS 6,949,571 B2 * 9/2005 Nagato et al. ............... 514/334
2007/0142640 A1   6/2007 Arimoto et al.

FOREIGN PATENT DOCUMENTS

EP           1 300 396 A1    9/2003
WO       WO-01/96308 A1    12/2001
WO     WO-2006/004107 A1    1/2006

OTHER PUBLICATIONS

Nerurkar et al., "Properties of Solids, etc.," Transport Processes in Pharmaceutical Systems, NY: Marcel Dekker, Inc., 2000, pp. 575-611.*
Hawley's Condensed Chemical Dictionary, p. 68 (1997).*
Lieberman et al., "Pharmaceutical dosage forms" p. 462-465 (1989).*
SSCI "Screening for amorphous drug, etc.," p. 1-3 (2003).*
SSCI "Amorphous solids, etc.," p. 1-3 (2003).*

* cited by examiner

*Primary Examiner*—Patricia L Morris
(74) *Attorney, Agent, or Firm*—Birch, Stewart, Kolasch & Birch, LLP

(57) ABSTRACT

An amorphous form of 3-(2-cyanophenyl)-5-(2-pyridyl)-1-phenyl-1,2-dihydropyridine-2-one.

3 Claims, 1 Drawing Sheet

AMORPHOUS FORM OF 1,2-DIHYDROPYRIDINE COMPOUND

TECHNICAL FIELD

This invention relates to amorphous form of 1,2-dihydropyridine compound [3-(2-cyanophenyl)-5-(2-pyridyl)-1-phenyl-1,2-dihydropyridin-2-one]which are provided with antagonistic action against AMPA (alpha-amino-3-hydroxy-5-methyl-4-isoxazolepropionic acid) receptor and/or inhibitory action against kainate receptor and which are useful as a therapeutic or prophylactic agent for neurodegenerative diseases or others, as well as their production process.

BACKGROUND ART 1,2-Dihydropyridine compounds possess antagonistic action against AMPA receptor and/or inhibitory action against kainate receptor and are useful as therapeutic or prophylactic agents for neurodegenerative diseases and others. Particularly, 3-(2-cyanophenyl)-5-(2-pyridyl)-1-phenyl-1,2-dihydropyridin-2-one (hereafter referred to as compound (1)) shows significant antagonistic action against AMPA receptor (see Patent Document 1).

Although Example 7 in Patent Document 1 discloses a process for producing the compound (1), there is merely described, "the residue is purified by silica gel column chromatography (ethyl acetate/hexane-1:2)" and there is no disclosure of the form of the obtained compound.
[Patent Document 1] WO/JP01/96308

DISCLOSURE OF THE INVENTION

Problems to be Solved by the Invention

The physical properties of medically useful form of compound such as crystal form or amorphous form affect medicament bioavailability, purity of drug substance, formulation design and the like. Thus, it is difficult to predict which crystal form or amorphous form of the compound is useful for pharmaceuticals in the development of pharmaceuticals. Therefore, there is a need for the finding of various crystal forms and amorphous forms useful as pharmaceuticals for each compound.

Means for Solving the Problems

As a result of the intensive and diligent studies, the present inventors found an amorphous form of compound (1) having excellent solubility in a solution such as JP2 fluid ("2nd fluid" as described in Disintegration Test of Japanese pharmacopoeia), upon which this invention has been completed.

Specifically, the present invention provides among others the following:

[1] An amorphous form of 3-(2-cyanophenyl)-5-(2-pyridyl)-1-phenyl-1,2-dihydropyridine-2-one.

[2] The amorphous form according to Item [1], having no diffraction peaks in an X-ray powder diffraction.

[3] A medicament comprising the amorphous form according to Item [1].

[4] A pharmaceutical composition comprising the amorphous form according to Item [1].

[5] A therapeutic or prophylactic agent for an acute neurodegenerative disease comprising the amorphous form according to Item [1].

[6] A therapeutic or prophylactic agent for neuropathy caused by acute phase of cerebrovascular disorder, head injury, spinal cord injury or hypoxia, or neuropathy caused by hypoglycemia, comprising the amorphous form according to Item [1].

[7] A therapeutic or prophylactic agent for a chronic neurodegenerative disease comprising the amorphous form according to Item [1].

[8] A therapeutic or prophylactic agent for Alzheimer's disease, Parkinson's disease, Huntington's chorea, amyotrophic lateral sclerosis or spinocerebellar degeneration, comprising the amorphous form according to Item [1].

[9] A therapeutic or prophylactic agent for epilepsy, hepatic encephalopathy, peripheral neuropathy, Parkinsonism, spastic paralysis, pain, neuralgia, schizophrenia, anxiety, drug-dependence, nausea, vomiting, dysuria, vision impairment caused by glaucoma, hearing impairment caused by antibiotics, or food poisoning, the agent comprising the amorphous form according to Item [1].

[10] A therapeutic or prophylactic agent for infectious encephalomyelitis, cerebrovascular dementia, or dementia or neurological symptom caused by meningitis, comprising the amorphous form according to Item [1].

[11] A therapeutic or prophylactic agent for a demyelinating disease comprising the amorphous form according to Item [1].

[12] The therapeutic or prophylactic agent according to Item [10], wherein the infectious encephalomyclitis is HIV encephalomyclitis.

[13] The therapeutic or prophylactic agent according to Item [11], wherein the demyelinating disease is encephalitis, acute sporadic encephalomyelitis, multiple sclerosis, acute polyradiculoneuropathy, Guillain-Barre syndrome, chronic inflammatory demyelinating polyradiculoneuropathy, Marchifava-Bignami disease, central pontomedullary myelinolysis, neuromyelitis optica, Devic's disease, Balo's disease, HIV-associated myclopathy, HTLV-associated myclopathy, progressive multifocal leukoencephalitis or a secondary demyelinating disease.

[14] The therapeutic or prophylactic agent according to Item [1,3], wherein the secondary demyclinating disease is CNS lupus erythematosus, polyarteritis nodosa, Sjoegren's syndrome, sarcoidosis or dissociated cerebral vasculitis.

According to the present invention, it has become possible that the compound (1) is produced as an amorphous form. The amorphous forms of the present invention have preferable properties and are suitable for use as an active ingredient of therapeutic or prophylactic agents for neurodegenerative diseases or others.

BEST MODES FOR CARRYING OUT THE INVENTION

Figure 1:
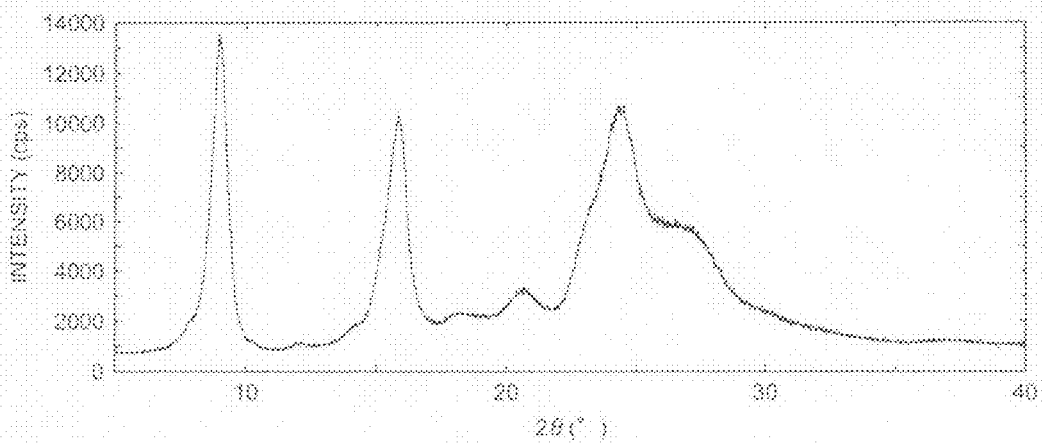
FIG. 1 shows an X-ray powder diffraction pattern of the crystals obtained in Reference Example A1.

This invention will be described in detail hereafter.
The compound (1) according to the present invention is an amorphous form with the characteristics of having no diffraction peaks in an X-ray powder diffraction.
[General Production Method of an Amorphous Form of Compound (1)]
An amorphous form of the present invention can be produced from a raw material of the compound (1) which is synthesized according to a method as described in the Example 7 of above-mentioned Patent Document 1 (WO/JP01/96308) or Production Example 4 shown below. An amorphous form of the compound (1) of the present invention can be stably synthesized by treating the compound (1) in the same matter of Example 1 shown below. It is difficult to produce an amorphous form of the present invention by the conventional production method such as freeze-drying.

Compound (1) used as a raw material can be in any form, i.e. can be hydrate or anhydrous form, amorphous or crystalline form (including plural crystal polymorphs), or a mixture thereof.

The use of the compound (1) as a therapeutic agent for neurodegenerative diseases or others is fully disclosed in Patent Document 1. The amorphous forms of the present invention can be used as the active ingredient in the therapeutic agent for neurodegenerative diseases or others. The entire disclosure of Patent Document 1 is thus hereby incorporated in this Specification by reference.

When the compound of this invention is to be used as a medicament, it is normally compounded with suitable pharmaceutical ingredients to prepare pharmaceutical products for use. Notwithstanding, the use of a drug substance form of the compound of the present invention as a medicament should not be negated.

The pharmaceutical ingredients may include excipients, binders, lubricants, disintegrating agents, coloring agents, taste correctives, emulsifiers, surfactants, dissolving aids, suspending agents, isotonizing agents, buffering agents, preservatives, antioxidants, stabilizers, absorption enhancers, and the like, all of which are generally used in medicaments. If desired, these agents may be combined for use.

The excipients may include, for example, lactose, white soft sugar, glucose, corn starch, mannitol, sorbitol, starch, alpha starch, dextrin, crystalline cellulose, light anhydrous silicic acid, aluminum silicate, calcium silicate, magnesium aluminometasilicate, calcium hydrogenphosphate, and the like.

The binders may include, for example, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

The lubricants may include, for example, magnesium stearate, calcium stearate, sodium stearyl fumarate, talc, polyethylene glycol, colloidal silica, and the like.

The disintegrating agents may include, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, and the like.

The coloring agents may include iron sesquioxide, yellow iron sesquioxide, carmine, caramel, beta-carotene, titanium oxide, talc, riboflavin sodium phosphate, yellow aluminum lake, and the like, which have been approved as additives for medicaments.

The taste correctives agents may include cocoa powder, menthol, aromatic powder, mentha oil, borneol, powdered cinnamon bark, and the like The emulsifiers or the surfactants may include stearyl triethanolamine, sodium lauryl sulfate, lauryl aminopropionic acid, lecithin, glycerin monostearate, sucrose fatty acid ester, glycerin fatty acid ester, and the like.

The dissolving aids may include polyethylene glycol, propylene glycol, benzyl benzoate, ethanol, cholesterol, triethanolamine, sodium carbonate, sodium citrate, Polysorbate 80, nicotinamide, and the like.

The suspending agents may include, in addition to the surfactants, hydrophilic polymers such as polyvinyl alcohol, polyvinylpyrrolidone, methylcellulose, hydroxymethylcellulose, hydroxyethylcellulose, and hydroxypropylcellulose.

The isotonizing agents may include glucose, sodium chloride, mannitol, sorbitol and the like.

The buffering agents may include the buffers of phosphate, acetate, carbonate, citrate and the like.

The preservatives may include methylparaben, propylparaben, chlorobutanol, benzyl alcohol, phenethyl alcohol, dehydroacetic acid, sorbic acid and the like.

The antioxidants may include sulfite, ascorbic acid, alpha-tocopherol and the like.

The stabilizers may include those generally used in medicaments.

The absorption enhancers may include those generally used in medicaments.

The pharmaceutical products described above may include: oral agents such as tablets, powders, granules, capsules, syrups, troches, and inhalations; external preparations such as suppositories, ointments, ophthalmic ointments, tapes, ophthalmic solutions, nasal drops, ear drops, poultices, and lotions; and injections.

The oral agents may appropriately be combined with the auxiliaries described above to form preparations. In addition, the surfaces of the agents may be coated if necessary.

The external preparations may appropriately be combined with the auxiliaries, in particular, excipients, binders, taste correctives, emulsifiers, surfactants, dissolving aids, suspending agents, isotonizing agents, preservatives, antioxidants, stabilizers, or absorption enhancers to form the preparations.

The injections may appropriately be combined with the auxiliaries, in particular, emulsifiers, surfactants, dissolving aids, suspending agents, isotonizing agents, preservatives, antioxidants, stabilizers, or absorption enhancers to form the preparations.

When the compound of this invention is to be used as a medicament, its dosage level may differ depending on the symptoms, ages or others. The compound is normally given in a single administration or in divided administrations 2 to 6 times daily at the following doses: from 0.05 to 10 mg (preferably from 0.1 to 5 mg) in the case of an oral agent; from 0.01 to 10 mg (preferably from 0.05 to 5 mg) in the case of an external preparation; and 0.01 to 5 mg in the case of an injection. Here, the actual amounts to be administered are indicated with respect to the oral agent and the injection, while the amount to be absorbed by the body is indicated with respect to the external preparation.

EXAMPLES

This invention will be specifically described in detail by way of the following examples; however, the present invention is not to be limited to these examples.

Production Example 1

Synthesis of 5-(2-pyridyl)-1-phenyl-1,2-dihydropyridin-2-one

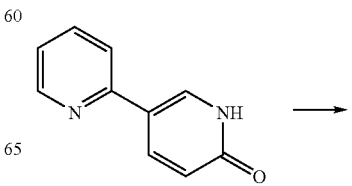

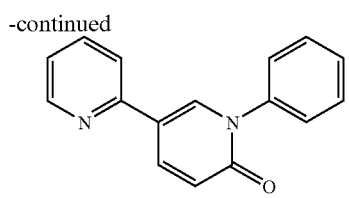

After a reactor was purged with nitrogen, a mixture of 5-(2-pyridyl)-1,2-dihydropyridin-2-one (7.33 kg: WO2004/009553), triphenylboroxine (9.0 kg), copper acetate (anhydrous) (0.80 kg), water (0.50 kg), pyridine (7.1 kg), and N,N-dimethylformamide (66.7 kg) was stirred in the reactor at an internal temperature of 28° C. for 1 hour.

While the air of which oxygen concentration was adjusted to 9% with nitrogen was blown into the reactor at a rate of 30 L/min, the reaction mixture was stirred at 39-40° C. (internal temperature) for 16 hours to yield reaction mixture 1A.

Water (191 kg) and 25% aqueous ammonia (85.8 kg) were charged in a separate reactor and cooled with cold water to 8.7° C. The reaction mixture 1A was then added to the reactor over 3 minutes. The reaction mixture was stirred for 4 hours at cooling with cold water. The precipitates in the reaction mixture were collected by filtration with a centrifuge and the filtrated residue was washed with 65 kg of water.

The precipitates, water (97 kg), and 25% aqueous ammonia (43.5 kg) were poured in a reactor and stirred for 1 hour while the temperature was maintained with warm water (25° C.). The precipitates in the reaction mixture were collected by filtration with a centrifuge and the filtrated residue was washed with 32.6 kg of water. The precipitates were then dried under reduced pressure (60° C.; 18 hours) to give 9.6 kg of 5-(2-pyridyl)-1-phenyl-1,2-dihydropyridin-2-one.

$^1$H NMR (400 MHz DMSO-$d_6$): δ 8.61-8.50 (m, 1H), 8.36 (d, 1H), 8.29 (dd, 1H), 7.90 (d, 1H), 7.80 (ddd, 1H), 7.56-7.45 (m, 5H), 7.27 (dd, 1H), 6.62 (d, 1H).

Production Example 2

Synthesis of 3-bromo-5-(2-pyridyl)-1-phenyl-1,2-dihydropyridin-2-one

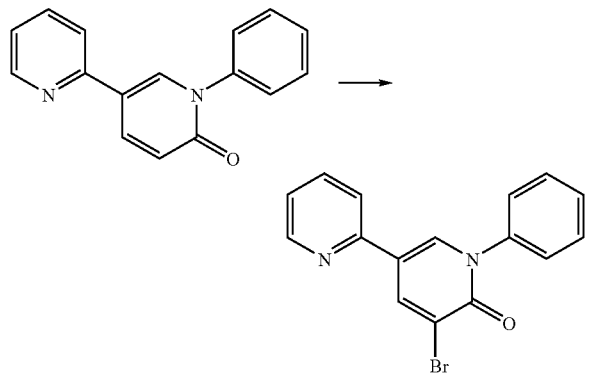

5-(2-Pyridyl)-1-phenyl-1,2-dihydropyridin-2-one (200 g), N-bromosuccinimide (157.7 g), and ethyl acetate (4 L) were added to a 10 L-reactor and the reaction mixture was stirred under a nitrogen stream at 30° C. (external temperature) for 9 hours and 20 minutes. 3% Hydrosulfite solution (2 L) and toluene (2 L) were added to the reaction mixture and then it was stirred at 55° C. (external temperature) for 30 minutes. After the completion of reaction, the aqueous layer (lower layer) in the reaction mixture was separated, and then, the organic layer was washed with water (2 L) four times. The solvent was evaporated at stirring under reduced pressure.

Subsequently, further addition of 1,2-dimethoxyethane (4 L) and concentration under reduced pressure gave a crude product of 3-bromo-5-(2-pyridyl)-1-phenyl-1,2-dihydropyridin-2-one.

Production Example 3

Synthesis of 3-(2-cyanophenyl)-5-(2-pyridyl)-1-phenyl-1,2-dihydropyridin-2-one

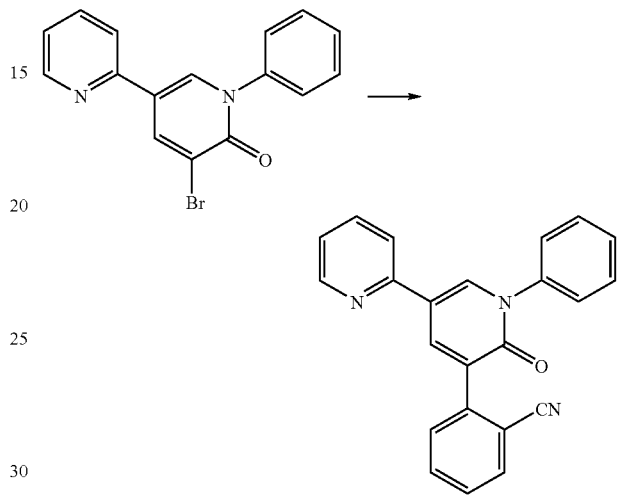

To the reactor containing the whole amount of the crude product of 3-bromo-5-(2-pyridyl)-1-phenyl-1,2-dihydropyridin-2-one obtained as the residue after concentration in Production Example 2 were added 2-(1,3,2-dioxaborinan-2-yl)benzonitrile (214.9 g), palladium acetate (3.44 g), triphenylphosphine (16.07 g), cuprous iodide (7.29 g), 1,2-dimethoxyethane (3.1 L) and potassium carbonate (158.8 g). Stirring at heating was carried out at 70° C. (external temperature) under a nitrogen atmosphere for 30 minutes and, then, at heating under reflux for 4 hours.

Subsequently, ethyl acetate (2.5 L) was added to the reaction mixture at 70° C. (external temperature) and the mixture was stirred for 10 minutes. The reaction mixture was filtrated and the filtrated residue was washed with ethyl acetate (2.5 L). This whole filtrate was transferred to a reactor, to which 12.5% aqueous ammonia (5 L) was further added. Stirring was carried out at 60° C. (external temperature) for 53 minutes. The lower layer (aqueous layer) in the reaction mixture was separated. 5% Brine (2.5 L) and 25% aqueous ammonia (2.5 L) were added to the remaining organic layer. After stirring, the lower (aqueous layer) was separated. 5% Brine (5 L) was further added to the remaining organic layer. After stirring, the lower (aqueous layer) was separated. The remaining organic layer was concentrated under reduced pressure, and then, acetone (4 L) was added, followed by concentration under reduced pressure.

Acetone (7.2 L) and water (0.8 L) were added to this residue, and it was dissolved by stirring at 60° C. (external temperature) for 1 hour and 10 minutes. Next, cooling was carried out at 38° C. (external temperature) for 18 minutes while stirring. To the reaction mixture was added 1 g of seed crystals, crystals of 3-(2-cyanophenyl)-5-(2-pyridyl)-1-phenyl-1,2-dihydropyridin-2-one hydrate. Stirring was carried out at 35° C. (external temperature) for 30 minutes. Subsequently, the reaction mixture was stirred at an external temperature being lowered by 5° C. every 30 minutes, and stirred at an external temperature of 10° C. for 17 hours.

Water (2.29 L) was added dropwise to the reaction mixture at stirring over a period of 3 hours and 10 minutes. After the addition, stirring continued for additional 1 hour and 20 minutes. The reaction mixture was filtrated and the filtrated residue was washed with 2 L of 50% acetone-water to give 3-(2-cyanophenyl)-5-(2-pyridyl)-1-phenyl-1,2-dihydropyridin-2-one (526.28 g) as a wet cake, which corresponded to 168.3 g as dry weight.

Production Example 4

3-(2-Cyano-phenyl)-5-(2-pyridyl)-1-phenyl-1,2-dihydropyridin-2-one (Hydrate Crystal)

A 10 L-flask was charged with 526.28 g of 3-(2-cyanophenyl)-5-(2-pyridyl)-1-phenyl-1,2-dihydropyridin-2-one obtained as the wet cake in Production Example 3. Out of an acetone-water prepared from 5890 mL of acetone and 490 mL of water, 5.5 L was added to the flask and heated. Filtration was carried out after dissolution. While the 10-L flask and the filtrated residue were washed with the remaining total of the acetone water, all the filtrate was transferred to a 10-L flask.

The mixture was stirred at an external temperature of 40° C., and after the internal temperature reached 40° C., the external temperature was adjusted to 35° C. Next, 842 mg of 3-(2cyanophenyl)-5-(2-pyridyl)-1-phenyl-1,2-dihydropyridin-2-one hydrate was added to the mixture. After stirring the mixture for 30 minutes, the external temperature was changed to 30° C., and then to 25° C. after 30 minutes. The external temperature was lowered by 5° C. every 30 minutes thereafter to as low as 15° C. After stirring the mixture at an external temperature of 15° C. for 30 minutes, the external temperature was further lowered to 8° C. and stirring continued for 1 hour.

To the mixture was added dropwise 842 mL of water at 11° C. (internal temperature) over a period of 1 hour and 10 minutes. One hour after the completion of addition, the external temperature was changed to 0° C. and the mixture was stirred for 40 minutes. The external temperature was then lowered to −20° C. and stirring continued for 15 hours.

The precipitates in the mixture were collected by filtration. After the precipitates were washed with 1700 mL of 50% acetone-water, they were dried under aeration for 50 minutes. Subsequently, these precipitates were dried with a vibration drier at 40° C. under reduced pressure for 11 hours and were additionally dried at 60° C. for 3 hours.

After the temperature of the drier was cooled to room temperature, the external atmosphere was aspirated into the drier at 950 hpa for 4 hours to give 172.4 g of 3-(2cyanophenyl)-5-(2-pyridyl)-1-phenyl-1,2-dihydropyridin-2-one (crystal form of the hydrate).

$^1$H NMR (400 MHz, DMSO-$d_6$): δ 8.61-8.57 (m, 1H), 8.53-8.52 (d-like, 1H), 8.47 (d, 1H), 8.01 (d, 1H), 7.92 (d, 1H), 7.86-7.81 (t-like, 1H), 7.79-7.76 (t-like, 1H), 7.72 (d, 1H), 7.61-7.48 (m, 6H), 7.31-7.28 (m, 1H).

Reference Example A1

Production of anhydrous crystals of 3-(2-cyanophenyl)-5-(2-pyridyl)-1-phenyl-1,2-dihydropyridin-2-one (Anhydrous Form II)

In the same manner as the procedure after reaction work-up that are described in Example 7 in WO01/96308, the production was carried out below. The synthetic method for 3-(2-cyanophenyl)-5-(2-pyridyl)-1-phenyl-1,2-dihydropyridin-2-one [alternative name: 2-(2-oxo-1-phenyl-5-(pyridin-2-yl)-1,2-dihydropyridin-3-yl)benzonitrile] is described in Example 7 in WO01/96308 as well as in Production Example 3 above.

Ethyl acetate (400 mL) was added to 3-(2-cyanophenyl)-5-(2-pyridyl)-1-phenyl-1,2-dihydropyridin-2-one (8 g). The mixture was heated at 60° C. in a warm bath. Additional acetate (160 mL) was added to the mixture and the solids were dissolved by heating at 70° C. in the warm bath. After n-hexane (80 mL) was added to this solution, the solvent was evaporated under reduced pressure to give 7.7 g of a pale yellow powder.

$^1$H NMR (400 MHz, DMSO-$d_6$): δ 8.59-8.57 (m, 1H), 8.53 (d, 1H), 8.47 (d, 1H), 8.01 (d, 1H), 7.92 (d, 1H), 7.83 (ddd, 1H), 7.80-7.76 (m, 1H), 7.73-7.71 (d-like, 1H), 7.61-7.48 (m, 6H), 7.30 (dd, 1H).

Example 1

3-(2-cyanophenyl-5-(2-pyridyl)-1-phenyl-1,2-dihydropyridin-2-one (Amorphous Form)

3-(2-Cyanophenyl)-5-(2-pyridyl)-1-phenyl-1,2-dihydropyridin-2-one (about 500 mg) were dissolved in 100 mL of acetone to prepare sample solution. This sample solution was spray-dried using Mini Spray Dryer B-290 manufactured by BUCHI under the conditions below to give 20 mg of a white solid (amorphous form).

[Conditions]

$N_2$ gas (Q-flow): 50 mm

ASPIRATOR (%): 100

Inlet temperature (° C.): 140

Pump (%): 40

Measurement of X-Ray Powder Diffraction Pattern

The X-ray powder diffraction of the compounds obtained in each Reference Example and Example were measured under the following measurement conditions according to the X-ray powder diffraction measurement method described in General Tests, Japanese Pharmacopeia.

(Equipment)

X-Ray Powder Diffraction Measurement Apparatus: RINT-2000 (from Rigaku Corporation)

(Operation Procedure)

A sample was ground using an agate mortar, taken on a glass plate having a diameter of 5 or 13 mm, and measured under the following conditions.

X-ray used: CuKα ray

Tube voltage: 40 kV

Tube current: 200 mA

Divergence slit: ½ deg

Receiving slit: 0.3 mm

Scattering slit: ½ deg

Scanning rate: 1 or 2°/min.

Scanning step: 0.02 or 0.01°

Measurement range (2θ): 5 to 40°

Figure 2:
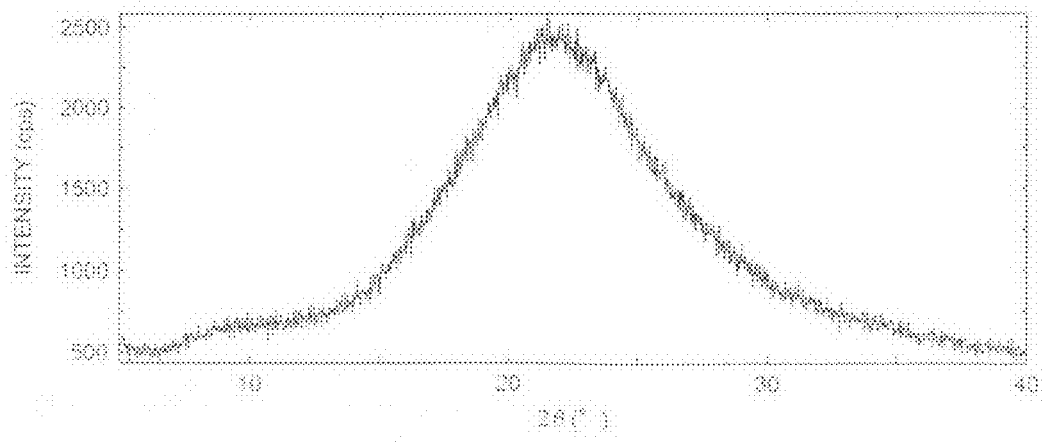
FIG. 2 shows an X-ray powder diffraction pattern of the amorphous form obtained in Example 1.

The X-ray powder diffraction pattern of the crystals obtained in Reference Example A1 is shown in FIG. 1, and the X-ray powder diffraction pattern of the amorphous form obtained in Example 1 is shown in FIG. 2.

Table 1 shows the peaks and their intensities at diffraction angles (2θ) for the crystals obtained in Reference Example A1.

Based on FIG. 2 that represents the X-ray powder diffraction pattern of the amorphous form obtained in Example 1, it can be found that the amorphous form obtained in Example 1 have no diffraction peaks in an X-ray powder diffraction.

TABLE 1

| PEAK NUMBER | 2θ | HALF WIDTH | D-VALUE | INTENSITY | RELATIVE INTENSITY |
|---|---|---|---|---|---|
| 1 | 9.010 | 0.588 | 9.8067 | 13370 | 100 |
| 2 | 15.850 | 0.682 | 5.5867 | 10137 | 76 |
| 3 | 24.390 | 0.847 | 3.6465 | 10672 | 60 |

Measurement of Solubility in JP2 Fluid after Shaking 5 minutes (Shake Flask Method)

[Operation Method]

Sample solutions were prepared by placing each sample (about 5 mg) in test tube, adding 5 mL of "2nd fluid" as described in General Tests (disintegration test) of Japanese Pharmacopeia (JP2 fluid: pH 6.8), and shaking 5 minutes at room temperature, followed by filtration. These sample solutions were analyzed using high performance liquid chromatography (HPLC), and calculated the concentration.

(HPLC Conditions)

HPLC System: LC-10AT System (from Shimadzu Corporation)

Detector: ultraviolet absorptiometer (wavelength: 290 nm)

Column: YMC Pack Pro C18, 4.6 mm I.D.×150 mm (from YMC, Japan)

Column temperature: 35° C.

Auto sampler temperature: 25° C.

Mobile phase:

A: water/acetonitrile/ammonium acetate (900:100:1, v/v/w)

B: water/acetonitrile/ammonium acetate (100:900:1, v/v/w)

A:B=600:400

(Isocratic Condition: B Concentration=40%)

Measuring time: 20 min.

Flow rate: 1.0 mL/min.

Injection amount: 50 μL

[Results]

Solubilities in JP2 fluid after shaking 5 minutes are shown in the following Table.

TABLE 2

| | Concentration (μg/mL) |
|---|---|
| Example 1 | 12.5 |
| Reference Example 1 | 4.8 |

INDUSTRIAL APPLICABILITY

The amorphous forms of the present invention have preferable properties and are suitable for use as an active ingredient of therapeutic or prophylactic agents for neurodegenerative diseases or the like.

The invention claimed is:

1. An amorphous form of 3-(2-cyanophenyl)-5-(2-pyridyl)-1-phenyl-1,2-dihydropyridine-2-one.

2. The amorphous form according to claim 1, having no diffraction peaks in an X-ray powder diffraction.

3. A pharmaceutical composition comprising:
the amorphous form according to claim 1; and
an inert carrier.

* * * * *